(12) United States Patent
Knudson et al.

(10) Patent No.: US 7,255,109 B2
(45) Date of Patent: *Aug. 14, 2007

(54) POLYMER PALATE IMPLANT

(75) Inventors: Mark B. Knudson, Shoreview, MN (US); Timothy R. Conrad, Eden Prairie, MN (US); Jerry C. Griffin, Chicago, IL (US)

(73) Assignee: Restore Medical, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/938,255

(22) Filed: Sep. 9, 2004

(65) Prior Publication Data

US 2005/0028830 A1    Feb. 10, 2005

Related U.S. Application Data

(63) Continuation of application No. 10/629,490, filed on Jul. 29, 2003, now Pat. No. 7,063,089, which is a continuation of application No. 09/872,545, filed on Jun. 1, 2001, now Pat. No. 6,626,181, which is a continuation of application No. 09/398,991, filed on Sep. 17, 1999, now Pat. No. 6,250,307.

(51) Int. Cl.
*A61B 19/00* (2006.01)
*A61F 5/56* (2006.01)

(52) U.S. Cl. ........................ 128/898; 128/848

(58) Field of Classification Search ........ 128/897–899, 128/846, 848, 859–862; 602/902; 623/9, 623/11.11, 4.11; 600/12, 23, 26
See application file for complete search history.

(56) References Cited

U.S. PATENT DOCUMENTS

| 3,998,209 A | 12/1976 | Macvaugh |
| 4,830,008 A | 5/1989 | Meer |
| 4,978,323 A | 12/1990 | Freedman |
| 5,046,512 A | 9/1991 | Murchie |
| 5,052,409 A | 10/1991 | Tepper |
| 5,133,354 A | 7/1992 | Kallok |
| 5,176,618 A | 1/1993 | Freedman |

(Continued)

FOREIGN PATENT DOCUMENTS

DE    38 30 481 A1    3/1990

(Continued)

OTHER PUBLICATIONS

Ersek et al, Minimally Invasive Macro Implants, 1996, Worldplast, vol. I/No. 4, pp. 275-285.*

(Continued)

*Primary Examiner*—Samuel G Gilbert
(74) *Attorney, Agent, or Firm*—Merchant & Gould P.C.

(57) ABSTRACT

A method and apparatus for treating snoring of a patient includes providing an implant for altering a dynamic response of a soft palate of the patient to airflow past the soft palate. The implant is embedded in the soft palate to alter the dynamic response. For example, the implant has a mass, stiffness or dampening sufficient to alter the dynamic response following the implantation without substantially impairing a function of the soft palate to close a nasal passage of the patient during swallowing.

1 Claim, 8 Drawing Sheets

U.S. PATENT DOCUMENTS

| | | | |
|---|---|---|---|
| 5,178,156 A | 1/1993 | Takishima et al. |
| 5,190,053 A | 3/1993 | Meer |
| 5,281,219 A | 1/1994 | Kallok |
| 5,284,161 A | 2/1994 | Karell |
| 5,456,662 A | 10/1995 | Edwards et al. |
| 5,514,131 A | 5/1996 | Edwards et al. |
| 5,540,733 A | 7/1996 | Testerman et al. |
| 5,591,216 A | 1/1997 | Testerman et al. |
| 5,674,191 A | 10/1997 | Edwards et al. |
| 5,718,702 A | 2/1998 | Edwards |
| 5,792,067 A | 8/1998 | Karell |
| 5,843,021 A | 12/1998 | Edwards et al. |
| RE36,120 E | 3/1999 | Karell |
| 5,897,579 A | 4/1999 | Sanders |
| 5,922,006 A | 7/1999 | Sugerman |
| 6,098,629 A | 8/2000 | Johnson et al. |
| 6,216,702 B1 | 4/2001 | Gjersøe |
| 6,250,307 B1 | 6/2001 | Conrad et al. |
| 6,401,717 B1 | 6/2002 | Conrad et al. |
| 6,450,169 B1 | 9/2002 | Conrad et al. |
| 6,626,181 B2 | 9/2003 | Knudson et al. |
| 6,634,362 B2 | 10/2003 | Conrad et al. |
| 6,679,918 B1 | 1/2004 | Benedict et al. |
| 6,748,950 B2 | 6/2004 | Clark et al. |
| 2004/0045556 A1 | 3/2004 | Nelson et al. |
| 2004/0134491 A1 | 7/2004 | Pflueger et al. |

FOREIGN PATENT DOCUMENTS

| | | |
|---|---|---|
| DE | 44 12 190 A1 | 10/1995 |
| DE | 199 20 114 A1 | 9/2000 |
| DE | 200 15 980 U1 | 3/2001 |
| EP | 0 706 808 A1 | 4/1996 |
| EP | 1 039 859 B1 | 12/2003 |
| SU | 1553140 | 3/1990 |
| WO | WO 00/59398 | 10/2000 |

OTHER PUBLICATIONS

Blumen, M. et al., "Radiofrequency Ablation for the Treatment of Mild to Moderate Obstructive Sleep Apnea," *The Laryngoscope*, vol. 112, pp. 2086-2092 (Nov. 2002).

Boot, H. et al., "Long-Term Results of Uvulopalatopharyngoplasty for Obstructive Sleep Apnea Syndrome", *The Laryngoscope*, pp. 469-475 (Mar. 2000).

Brietzke, S. et al., "Injection snoreplasty: How to treat snoring without all the pain and expense," *Otolaryngology*, vol. 124, No. 5, pp. 503-510 (May. 2001).

Brochure, "Snoreless™", *Nutrition for Life International*, 2 pgs. (Dec. 1999).

C. Lorenz, "If he Snores—what can you do about it?", Today's Woman, Jul. 1948, p. 112.

Cole, P. et al., "Snoring: A Review and a Reassessment", *The Journal of Otolaryngology*, vol. 24, No. 5, pp. 303-306 (1995).

Coleman, S. et al., "Midline Radiofrequency Tissue Reduction of the Palate for Bothersome Snoring and Sleep-Disordered Breathing: A Clinical Trial", *Otolaryngology-Head and Neck Surgery*, pp. 387-394 (Mar. 2000).

Dalmasso, F. et al., "Snoring: analysis, measurement, clinical implications and applications", *Eur. Respir. J.*, vol. 9, pp. 146-159 (1996).

Ellis, P. D. M. et al., "Surgical relief of snoring due to palatal flutter: a preliminary report", *Annals of the Royal College of Surgeons of England*, vol. 75, No. 4, pp. 286-290 (1993).

Fischer, Y. et al., "Die Radiofrequenzablation des weichen Gaumens (Somnoplastik)", *Redaktion*, pp. 33-40 (2000).

Harries, P.G. et al., "Review Article: The surgical treatment of snoring", *The Journal of Laryngology and Otology*, vol. 110, pp. 1105-1106 (Dec. 1996).

Huang, L. et al., "Biomechanics of snoring", *Endeavour*, vol. 19, No. 3, pp. 96-100 (1995).

Huang, L. et al., "Flutter of Cantilevered Plates in Axial Flow", *Journal of Fluids and Structures*, vol. 9, pp. 127-147 (1995).

International Search Report for Application No. PCT/US00/26616 dated Dec. 14, 2000.

International Search Report for Application No. PCT/US00/40830 dated Feb. 6, 2001.

Kasey, K. et al., "Radiofrequency Volumetric Reduction of the Palate: An Extended Follow-Up Study", *Otolaryngology-Head and Neck Surgery*, vol. 122, No. 3, pp. 410-414 (Mar. 2000).

LaFrentz et al., "Palatal Stiffening Techniques for Snoring in a Novel Canine Model", Abstracts of the Twenty-Second Annual MidWinter Meeting of the Association for Research in Otolaryngology, Abstract No. 499, vol. 22, pp. 125-126 (Feb. 13-18, 1999).

Schwartz, R.S. et al., "Effects of electrical stimulation to the soft palate on snoring and obstructive sleep apnea", *J. Prosthet. Dent.*, vol. 76, No. 3, pp. 273-281 (1996).

Wiltfang, J. et al., "First results on daytime submadibular electrostimulation of suprahyoidal muscles to prevent night-time hypopharyngeal collapse in obstructive sleep apnea syndrome", *Int. J. Oral Maxillofac. Surg.*, vol. 28, pp. 21-25 (1999).

\* cited by examiner

POLYMER PALATE IMPLANT

This application is a continuation of U.S. patent application Ser. No. 10/629,490 filed Jul. 29, 2003 now U.S. Pat. No. 7,063,089, which is a continuation of U.S. patent application Ser. No. 09/872,545 filed Jun. 1, 2001, now U.S. Pat. No. 6,626,181; which is a continuation of U.S. patent application Ser. No. 09/398,991 filed Sep. 17, 1999, now U.S. Pat. No. 6,250,307; which applications are incorporated herein by reference.

BACKGROUND

1. Field of the Invention

This invention is directed to methods and apparatuses for treating snoring.

2. Description of the Prior Art

Snoring has received increased scientific and academic attention. One publication estimates that up to 20% of the adult population snores habitually. Huang, et al., "Biomechanics of Snoring", *Endeavour*, p. 96-100, Vol. 19, No. 3(1995). Snoring can be a serious cause of marital discord. In addition, snoring can present a serious health risk to the snorer. In 10% of habitual snorers, collapse of the airway during sleep can lead to obstructive sleep apnea syndrome. Id.

Notwithstanding numerous efforts to address snoring, effective treatment of snoring has been elusive. Such treatment may include mouth guards or other appliances worn by the snorer during sleep. However, patients find such appliances uncomfortable and frequently discontinue use (presumably adding to marital stress).

Electrical stimulation of the soft palate has been suggested to treat snoring and obstructive sleep apnea. See, e.g., Schwartz, et al., "Effects of electrical stimulation to the soft palate on snoring and obstructive sleep apnea", *J. Prosthetic Dentistry*, pp. 273-281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Electrical stimulation to treat sleep apnea is discussed in Wiltfang, et al., "First results on daytime submandibular electrostimulation of suprahyoidal muscles to prevent night-time hypopharyngeal collapse in obstructive sleep apnea syndrome", *International Journal of Oral & Maxillofacial Surgery*, pp. 21-25 (1999).

Surgical treatments have been employed. One such treatment is uvulopalatopharyngoplasty. In this procedure, so-called laser ablation is used to remove about 2 cm of the trailing edge of the soft palate thereby reducing the soft palate's ability to flutter between the tongue and the pharyngeal wall of the throat. The procedure is frequently effective to abate snoring but is painful and frequently results in undesirable side effects. Namely, removal of the soft palate trailing edge comprises the soft palate's ability to seal off nasal passages during swallowing and speech. In an estimated 25% of uvulopalatopharyngoplasty patients, fluid escapes from the mouth into the nose while drinking. Huang, et al., supra at 99. Uvulopalatopharyngoplasty (UPPP) is also described in Harries, et al., "The Surgical treatment of snoring", *Journal of Laryngology and Otology*, pp. 1105-1106 (1996) which describes removal of up to 1.5 cm of the soft palate. Assessment of snoring treatment is discussed in Cole, et al., "Snoring: A review and a Reassessment", *Journal of Otolaryngology*, pp. 303-306 (1995).

Huang, et al., supra, describe the soft palate and palatal snoring as an oscillating system which responds to airflow over the soft palate. Resulting flutter of the soft palate (rapidly opening and closing air passages) is a dynamic response generating sounds associated with snoring. Huang, et al., propose an alternative to uvulopalatopharyngoplasty. The proposal includes using a surgical laser to create scar tissue on the surface of the soft palate. The scar is to reduce flexibility of the soft palate to reduce palatal flutter. Huang, et al., report initial results of complete or near-complete reduction in snoring and reduced side effects.

Surgical procedures such as uvulopalatopharyngoplasty and those proposed by Huang, et al., continue to have problems. The area of surgical treatment (i.e., removal of palatal tissue or scarring of palatal tissue) may be more than is necessary to treat the patient's condition. Surgical lasers are expensive. The proposed procedures are painful with drawn out and uncomfortable healing periods. The procedures have complications and side effects and variable efficacy (e.g., Huang, et al., report promising results in 75% of patients suggesting a full quarter of patients are not effectively treated after painful surgery). The procedures may involve lasting discomfort. For example, scar tissue on the soft palate may present a continuing irritant to the patient. Importantly, the procedures are not reversible in the event they happen to induce adverse side effects not justified by the benefits of the surgery.

SUMMARY OF THE INVENTION

According to a preferred embodiment of the present invention, methods and apparatuses are disclosed for treating snoring of a patient. The invention includes providing an implant for altering a dynamic response of a soft palate of the patient to airflow past the soft palate. The implant is embedded in the soft palate to alter the dynamic response. For example, the implant has a mass, stiffness or dampening sufficient to alter the dynamic response following the implantation without substantially impairing a function of the soft palate to close a nasal passage of the patient during swallowing.

DESCRIPTION OF THE PREFERRED EMBODIMENT

For ease of understanding the present invention, the dynamics of snoring are explained with reference to FIGS. 1-4. The hard palate HP overlies the tongue T and forms the roof of the mouth M. The hard palate HP includes a bone support B and does not materially deform during breathing. The soft palate SP is soft and is made up of mucous membrane, fibrous and muscle tissue extending rearward from the hard palate HP. A leading end LE of the soft palate SP is anchored to the trailing end of the hard palate HP. A trailing end TE of the soft palate SP is unattached. Since the soft palate SP is not structurally supported by bone or hard cartilage, the soft palate SP droops down from the plane of the hard palate HP in an arcuate geometry of repose.

The pharyngeal airway passes air from the mouth M and the nasal passages N into the trachea TR. The portion of the pharyngeal airway defined between opposing surfaces of the upper surface of the soft palate SP and the wall of the throat is the nasopharynx NP.

Figure 1:
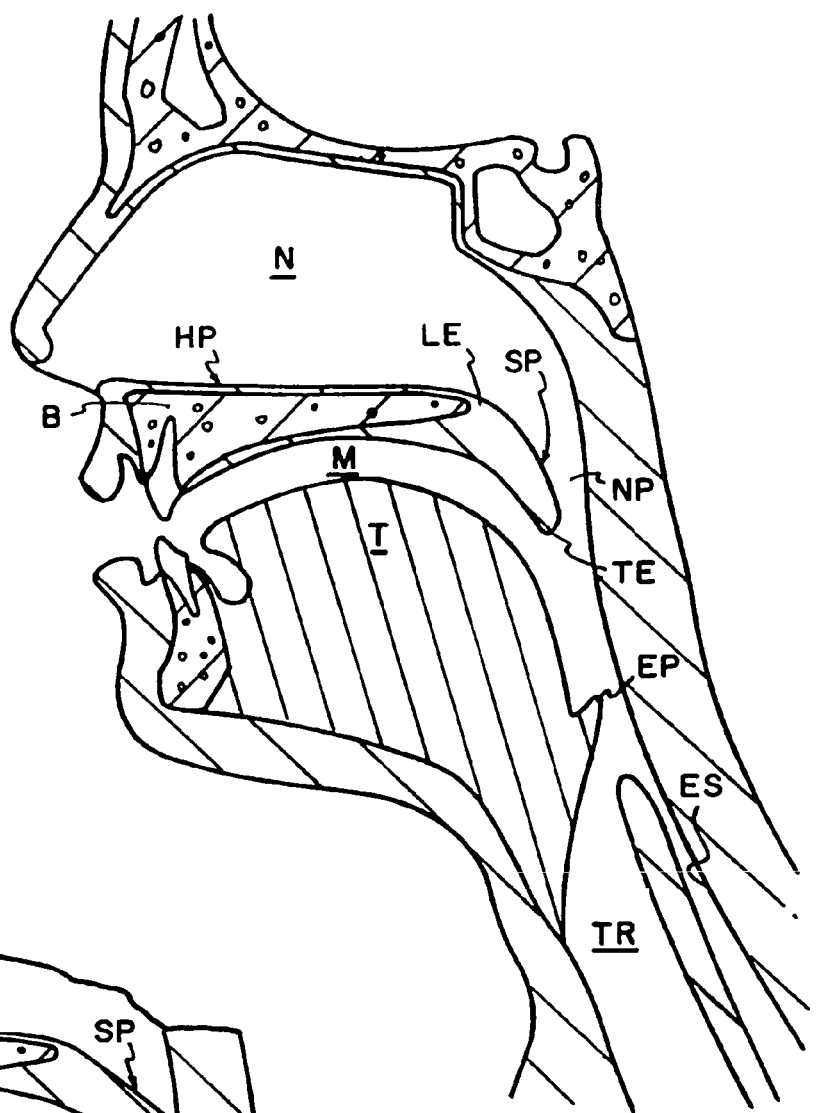
FIG. 1 is a side sectional view of a portion of a human head showing a soft palate in a relaxed state and in relation in adjacent anatomical features.

During normal breathing, the soft palate SP is in the relaxed state shown in FIG. 1 with the nasopharynx NP unobstructed and with air free to flow into the trachea TR from both the mouth M and the nostrils N.

Figure 2:
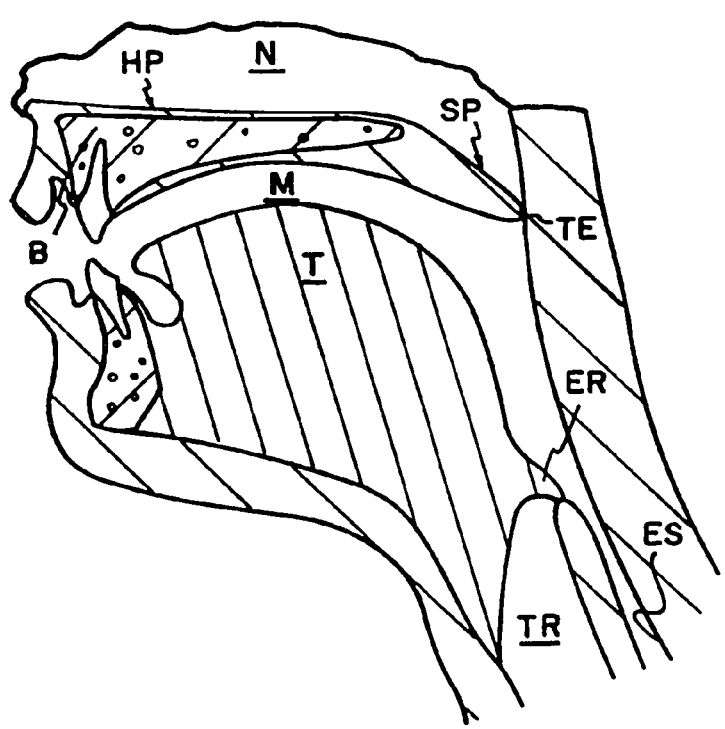
FIG. 2 is a portion of the view of FIG. 1 showing the soft palate in a flexed state.

During swallowing, the soft palate SP flexes and extends (as shown in FIG. 2) to close the nasopharynx NP thereby preventing fluid flow from the mouth M to the nasal passages N. Simultaneously, the epiglottis EP closes the trachea TR so that food and drink pass only into the esophagus ES and not the trachea TR. The soft palate SP is a valve to prevent regurgitation of food into the nose N. The soft palate SP also regulates airflow through the nose N while talking. Since the soft palate SP performs such important functions, prior art techniques for surgically altering the soft palate SP can compromise these functions.

The majority of snoring is caused by the soft palate SP flapping back and forth. If breathing is solely through the nose N with the mouth closed, the trailing edge TE of the soft palate SP is sucked into the nasopharyngeal space NP obstructing the airway and subsequently falls opening the airway in a repeating cycle. When the mouth is open, air flows over the upper and lower surfaces of the soft palate SP causing the soft palate SP to flap up and down alternating in obstructing the oral and nasal passageways M, N. The snoring sound is generated by impulses caused by rapid obstruction and opening of airways. Huang, et al., state the airway passage opening and closing occurs 50 times per second during a snore. Huang, et al., utilize a spring-mass model (FIG. 5) to illustrate oscillation of the soft palate in response to airflow (where the soft palate is the ball B of mass depending by a spring S from a fixed anchor A).

Figure 3:
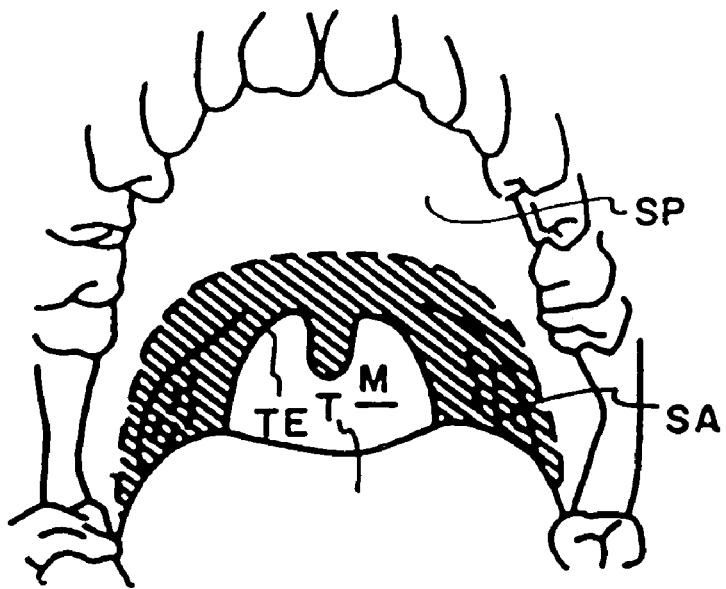
FIG. 3 is a front view of an interior of the mouth shown in FIG. 1 and showing an area to be ablated according to a first prior art surgical procedure.
Figure 4:
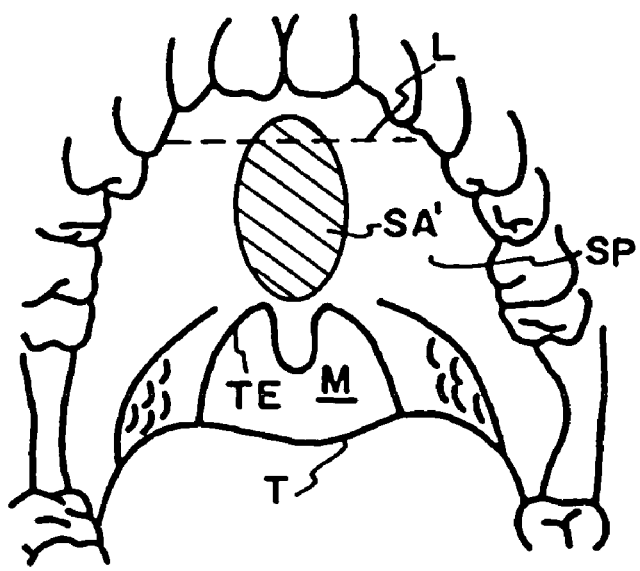
FIG. 4 is the view of FIG. 3 and showing an area to be scarred according to a second prior art surgical procedure.

Huang, et al., analogize the shortening of the soft palate SP in uvulopalatopharyngoplasty as effectively raising the critical air flow speed at which soft palate flutter will occur. The shaded area SA in FIG. 3 shows the area of the trailing end TE of the soft palate SP to be removed during this procedure. The alternative procedure proposed by Huang, et al., reduces the flexibility of the soft palate SP through surface scarring which is asserted as effecting the critical flow speed. The shaded area SA' in FIG. 4 shows the area to be scarred by this alternate procedure. In FIG. 4, dashed line L shows the demarcation between the soft and hard palates.

Figure 5:
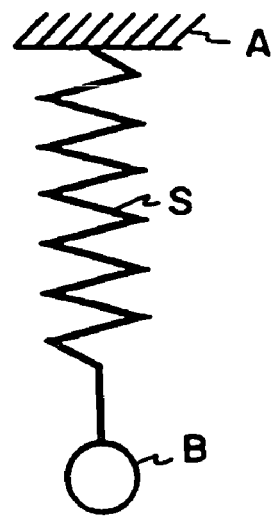
FIG. 5 is a schematic representation of a spring-mass system model of the soft palate.

Using the spring-mass model of FIG. 5 as a convenient model of the soft palate SP, the present invention is directed to a surgical implant into the soft palate SP to alter the elements of the model and thereby alter the dynamic response of the soft palate SP to airflow. The implant can alter the mass of the model (the ball B of FIG. 5), the spring constant of the spring S, the dampening of the spring S or any combination of these elements. Unlike the prior art surgical techniques, the implants that will be described are easy to insert in a small incision resulting in reduced patient discomfort and are not exposed to the interior of the mouth (such as the surface scarring of Huang, et al.) as a patient irritant. Also, as will be described, the degree of dynamic remodeling can be fine tuned avoiding the need for excessive anatomical modification and are reversible in the event of adverse consequences.

Figure 6:
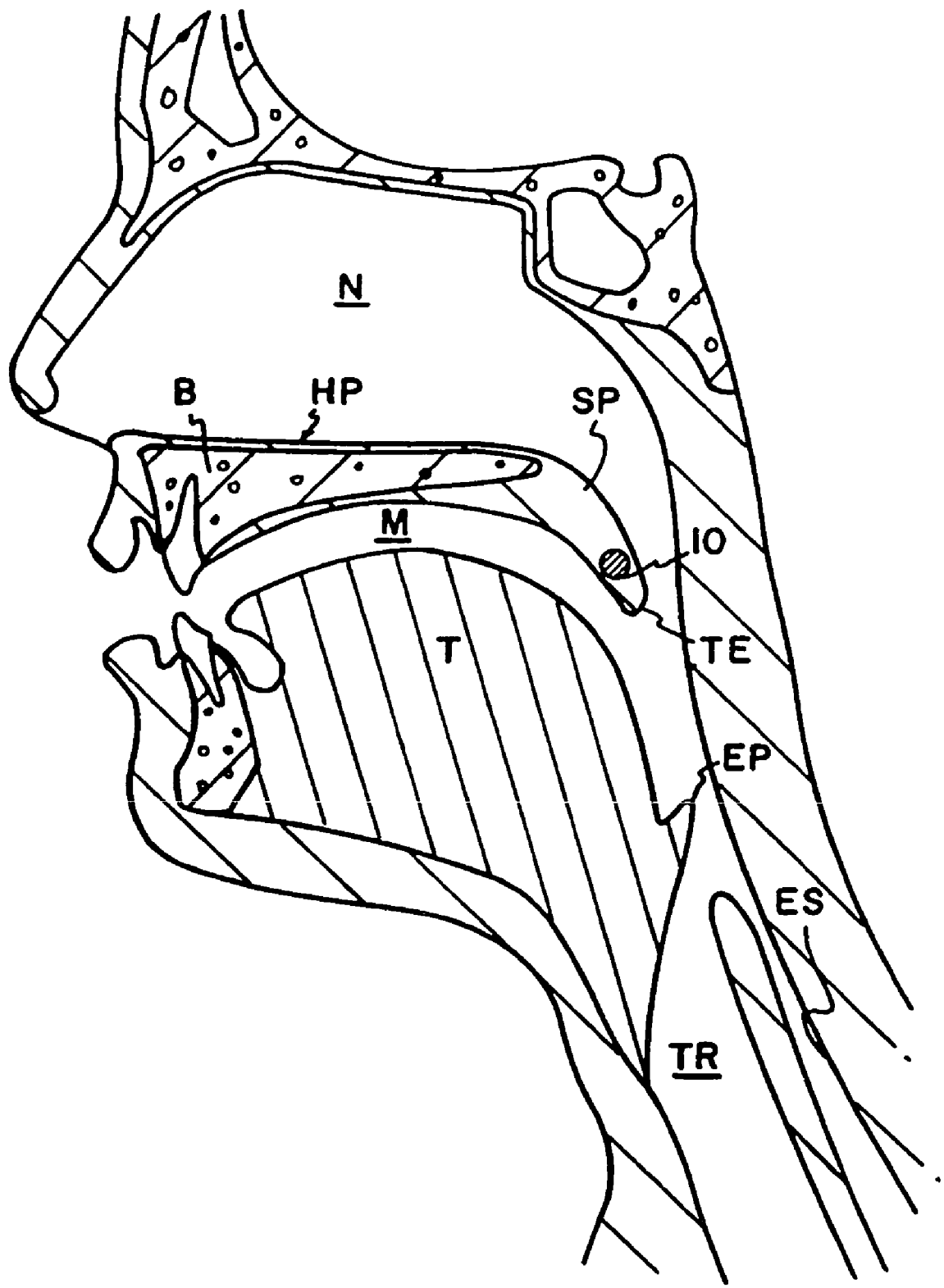
FIG. 6 is the view of FIG. 1 with the soft palate containing an implant according to a first embodiment of the present invention.
Figure 7:
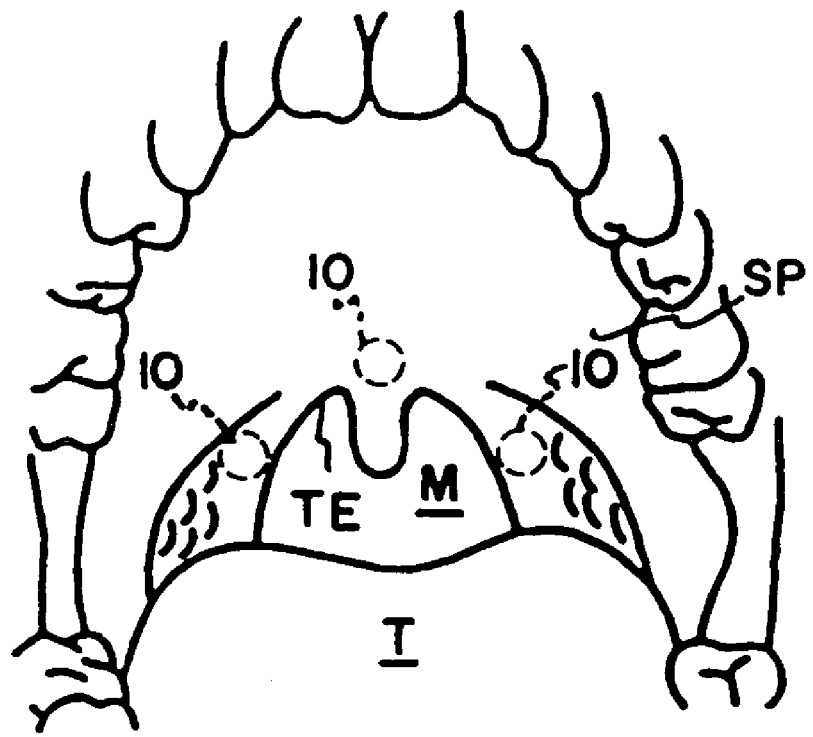
FIG. 7 is the view of FIG. 3 showing the embodiment of FIG. 6.
Figure 8:
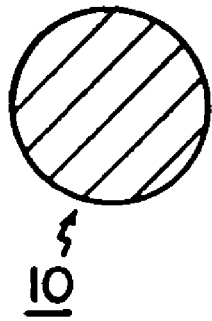
FIG. 8 is a cross-sectional view of the implant of FIG. 6.

FIGS. 6-7 illustrate a first embodiment of the present invention where individual units 10 of mass (in the form of implantable modular devices such as spheres or implants of other geometry) are imbedded in the soft palate SP in close proximity to the trailing end TE. With reference to the model of FIG. 5, the spheres add mass to the mass-spring system thereby altering dynamic response to airflow and adding resistance to displacement and accelerating. The placement of the units 10 of mass also alter the location of the soft palate's center of mass further altering the model and dynamic response.

The embodiment of FIGS. 6-10 is tunable to a particular patient in that multiple modules 10 can be implanted (as illustrated in FIG. 7). This permits the surgeon to progressively increase the number of implanted modules 10 until the altered dynamic response is such that snoring inducing oscillation is abated at normal airflow. The individual modules 10 may be placed into the soft palate SP through small individual incisions closed by sutures which is much less traumatic than the gross anatomical destruction of uvulopalatopharyngoplasty or the large surface area scarring proposed by Huang, et al.

Preferably, such modules 10 of mass are solid modules such as spheres of biocompatible material which are radiopaque (or radio-marked) and compatible with magnetic resonance imaging (MRI). Titanium is such a material. By way of non-limiting example, the modules 10 of mass may be about 2-4 mm in diameter. In the case of pure, non-sintered titanium, each such sphere 10 would add 0.15-1.22 gm of mass to the trailing end TE of the soft palate SP and contribute to re-modeling the mass distribution of the soft palate SP. An example of an alternative material is any biocompatible ceramic.

Figure 9:
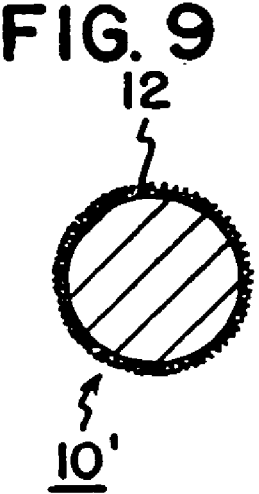
FIG. 9 is a first modification of the implant of FIG. 8 having a tissue in-growth layer.

As shown in FIG. 9, the spheres (labeled 10' to distinguish from the version 10 of FIG. 8) may be sintered throughout or otherwise provided with tissue growth inducing material 12 on their outer surface. Such material may be a sintered outer layer or a coating or covering such as a polyester fabric jacket. Such material permits and encourages tissue in-growth to secure the implant 10' in place. Also, placement of an implant 10 or 10' will induce a fibrotic response acting to stiffen the soft palate SP (and further alter the dynamic response and resistance to displacement and acceleration). A sintered or coated sphere 10' will enhance the fibrotic response and resulting stiffening.

Figure 10:
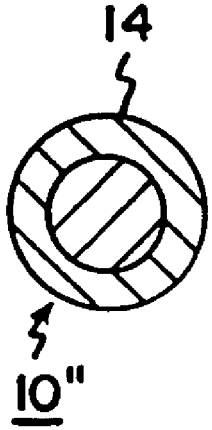
FIG. 10 is a second modification of the implant of FIG. 8 having a smooth outer layer.

While tissue in-growth and enhanced fibrotic response have the benefits described above, such embodiments may make the implant 10' more difficult to remove in the event reversal of the procedure is desired. Therefore, as shown in FIG. 10 as an alternative, the spheres (labeled 10'' to distinguish from the implants 10, 10') maybe coated with smooth coating 14 (such as parylene or PTFE) to reduce fibrosis.

The embodiments of FIGS. 6-10 add to and relocate the mass of the spring-mass system of FIG. 5 to remodel the dynamic response. The amount of mass is selected to alter the dynamic response but not preclude the soft palate SP being moved to close off nasal passages N during swallowing. Through fibrotic response and incision healing, the spring S of the model is stiffened.

In addition to modifying the mass profile of the spring-mass system, the spring component S of FIG. 5 can be modified (alone or in combination with mass modification) to alter dynamic response. FIG. 11-16 illustrate an implant 20 in the form of a flexible strip for placement in the soft palate. The use of the term "strip" herein is not intended to be limited to long, narrow implants but can also include plates or other geometries implanted to alter the dynamic model of the soft palate SP. Elongated strips are presently anticipated as a preferred geometry to facilitate ease of implant.

Figure 11:
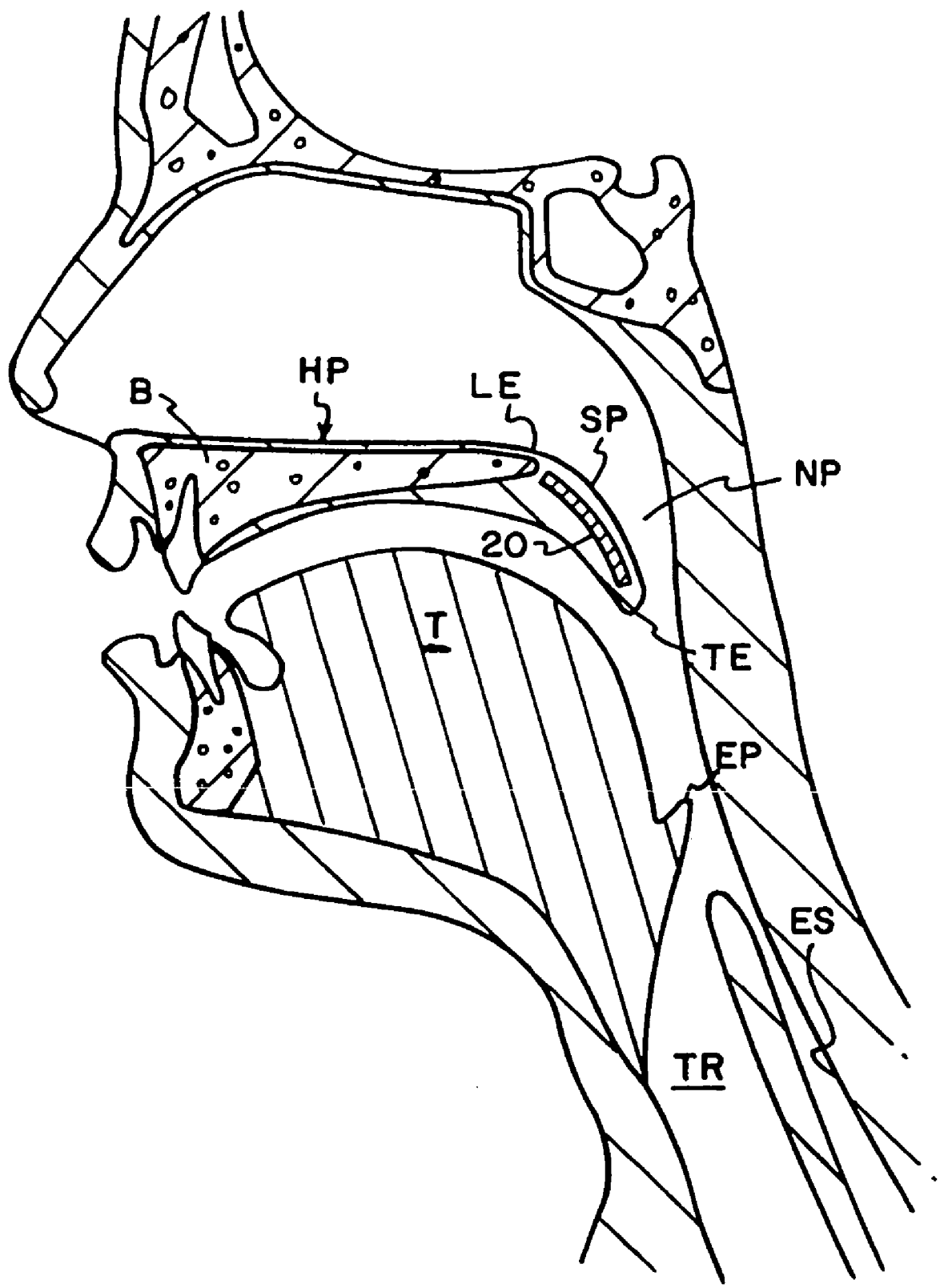
FIG. 11 is the view of FIG. 6 with the soft palate containing an implant according to a second embodiment of the present invention.
Figure 12:
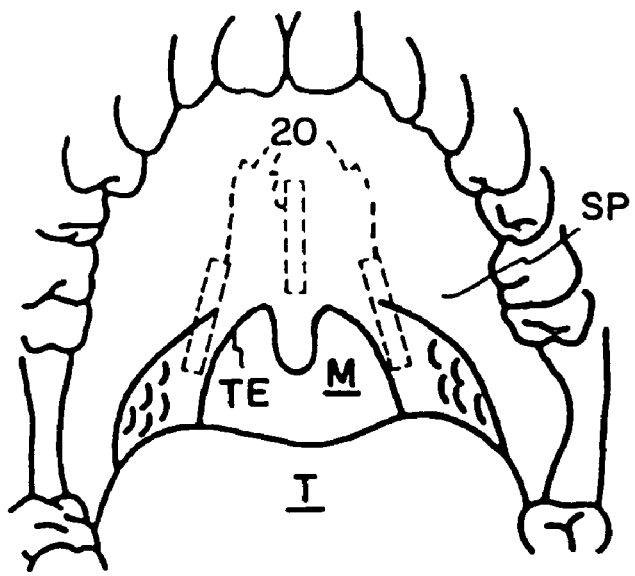
FIG. 12 is the view of FIG. 7 showing the embodiment of FIG. 11.

The strip 20 has a transverse dimension less than a longitudinal dimension. By way of non-limiting example, the strip may have a length $L_S$ of about 20-30 mm, a thickness $T_S$ of about 2-4 mm and a width $W_S$ of 5-10 mm. As shown in FIG. 11, the strip 20 is embedded in the soft palate SP with the longitudinal dimension $L_S$ extending from adjacent the hard palate HP toward the trailing end TE of the soft palate SP. As shown in FIG. 12, multiple strips 20 may be embedded in the soft palate SP extending either straight rearward or angled to the sides while extending rearward. The strips 20 may be formed straight (FIG. 14) or pre-shaped (FIG. 15) to have a rest shape approximate to the side-cross section shape of the soft palate in a relaxed state.

Figure 16:
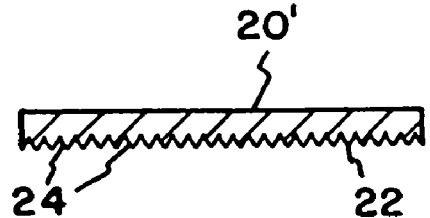
FIG. 16 is the view of FIG. 14 with the implant constructed to have greater flexion in a downward direction.

The strips 20 may be any flexible, biocompatible material and are preferably radiopaque or radio-marked as well as MRI compatible. The strips 20 need not be elastic and having a material spring constant biasing them to their original shape. Such strips 20 could simply be flexible, plastically deformable strips which are stiffer than the soft palate SP to reinforce the soft palate SP and assist the soft palate SP in resisting deflection due to airflow. Such stiffening of the soft palate SP stiffens and dampens the spring S in the spring-mass system of FIG. 5 and alters the dynamic response of the soft palate SP. The strip 20 may be a spring having a spring constant to further resist deflection of the soft palate SP as well as urging the soft palate SP to the relaxed state of FIG. 5. The stiffness of the strip 20, a spring constant of the strip 20, and the number of strips 20, are selected to avoid preclusion of closure of the soft palate SP during swallowing. Examples of suitable materials include titanium and nitinol (a well-known nickel-titanium alloy). As with the examples of FIGS. 9 and 10, the strips 20 may be provided with tissue in-growth surfaces or may be coated as desired. Also, the strips may be structurally modified to control their flexibility. In FIG. 16, the bottom 22 of the strip 20 (facing the tongue after placement) is provided with transverse notches 24 to enhance downward flexion of the strip 20 relative to upward flexion of the strip 20 following placement.

Figure 13:
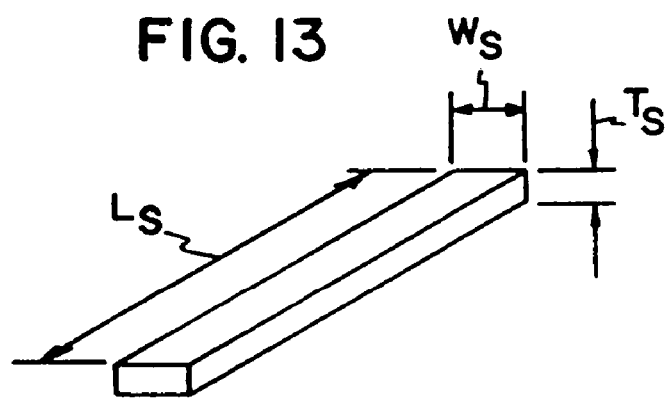
FIG. 13 is a perspective view of the implant of FIG. 11.
Figure 14:
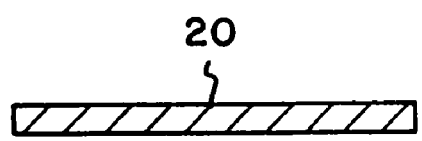
FIG. 14 is a cross-sectional view of the implant of FIG. 13.
Figure 15:
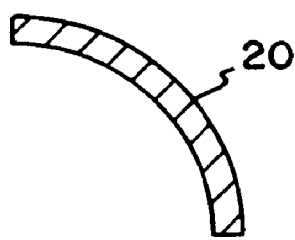
FIG. 15 is a view of the implant of FIG. 14 with the implant pre-formed to assume the shape of a soft palate in a relaxed state.
Figure 17:
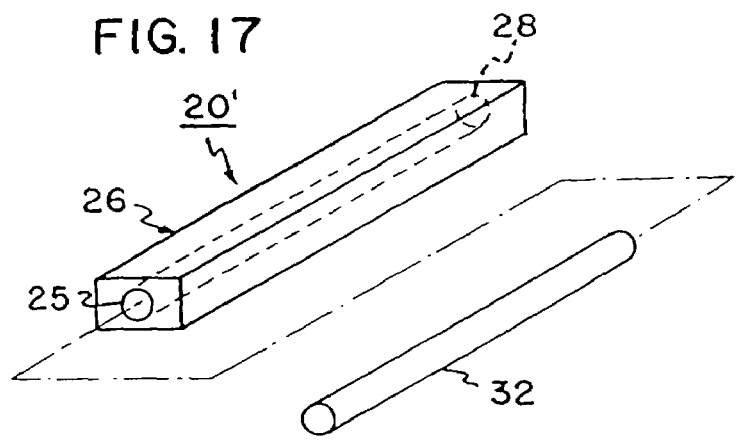
FIG. 17 is an exploded perspective view of first modification of the implant of FIG. 13.

FIG. 17 provides an alternative to the strips 20 of FIG. 13. In FIG. 17, the strip 20' includes a housing 26 having an interior space 28 with an access opening 25. Tne interior space 28 extends in the longitudinal dimension of the housing 26. The strip 20' further includes a longitudinal insert 32 sized to be passed through the access opening 25 and into the space 28. By way of non-limiting example, the housing 26 could be silicone rubber (with radio-markers, not shown, to indicate placement) and the inserts 32 could be titanium rods or other flexible member. With the embodiment of FIG. 17, the housing 26 (without an insert) may be embedded in the soft palate SP. The housing 26 acts independently as a stiffening strip to add stiffness to the soft palate SP to alter the soft palate's dynamic response. In the event further stiffening or a spring action is desired, the implant 20' can be selectively tuned to the patient's unique dynamic model by placing the insert 32 into the space 28 at the time of initial surgery or during a subsequent procedure. The embodiment of FIG. 17, permits selection of an insert 32 from a wide variety of materials and construction so that an insert 32 of desired characteristics (e.g., stiffness and spring action) can be selected to be inserted in the space 28 and alter the dynamic response as desired. The embodiment of FIG. 17 also permits later removal of the insert 32 and replacement with a different insert 32 of different properties for post-surgery modification of the soft palate's dynamic response.

Figure 18:
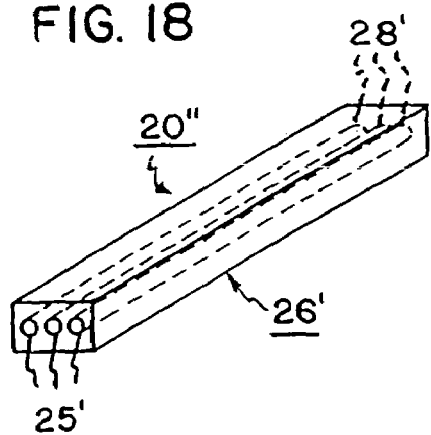
FIG. 18 is a perspective view of a modification of a housing of the embodiment of FIG. 17.

The embodiment of FIG. 18 is similar to that of FIG. 17. The housing 26' is provided with multiple, parallel-aligned interior spaces 28' and access openings 25'. In addition to the function and benefits of the embodiment of FIG. 17, the number of inserts 32 may be varied to alter and adjust the dynamic response of the soft palate SP.

Figure 19:
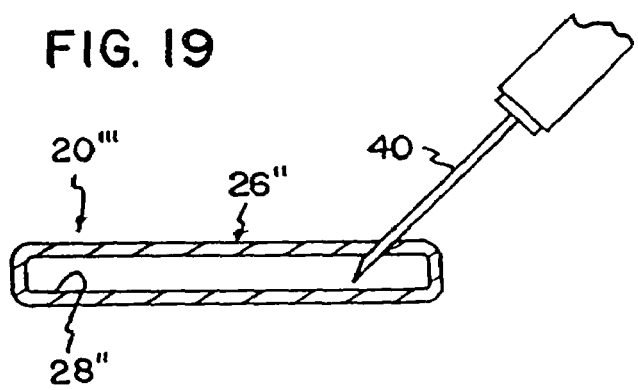
FIG. 19 is a side section view of a second modification of the implant of FIG. 13.
Figure 20:
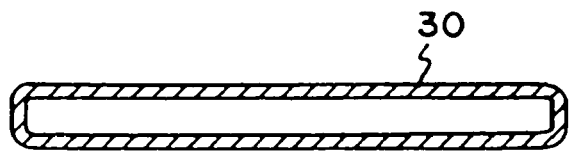
FIG. 20 is a cross-sectional view of an implant that is another embodiment of the present invention, the implant is shown in a flattened orientation.

FIG. 19 illustrates a still further embodiment of the strip implant. In FIG. 19, the strip 20''' is a bladder having a housing 26'' in the form of a completely sealed envelope of flexible synthetic material defining an interior space 28''. The envelope 26'' is preferably self-sealing following needle injection. Fluid is injected into the housing 26''(e.g., through hypodermic needle 40 injection) to stiffen the strip 20'''. Addition of fluid further stiffens the strip 20''' and further alters the dynamic response of the soft palate SP. Removal of fluid increases the flexibility. Unlike the embodiments of FIG. 17 (where inserts 32 are most effectively replaced post-operatively through incision to alter flexibility), the embodiment of FIG. 19 permits selectively varying flexibility of the soft palate SP through needle injection. An alternative to FIG. 19 is to fill the space 28'' with a so-called phase change polymer and inject a stiffening agent into the space 28'' to alter the flexibility of the polymer.

FIGS. 20-23 illustrate a still further embodiment of the present invention. In the foregoing embodiments, the spring-mass system of FIG. 5 is altered by altering the mass of the soft palate SP or the spring characteristics of the soft palate SP. The dynamic response can also be altered by altering the force acting on the spring-mass system. Namely, the force acting on the soft palate SP is generated by airflow over the surface of the soft palate. The soft palate acts as an airfoil which generates lift in response to such airflow. By modifying the longitudinal (i.e., anterior to posterior) cross-sectional geometry of the soft palate SP, the aerodynamic response and, accordingly, the dynamic response are altered.

Figure 21:
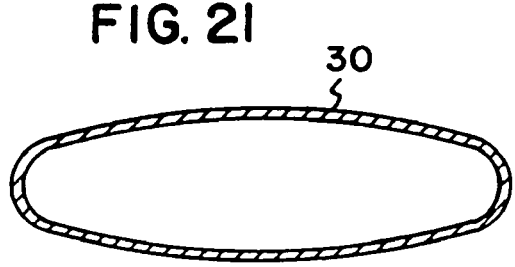
FIG. 21 is a cross-sectional view of the implant of FIG. 20 in an expanded orientation.
Figure 22:
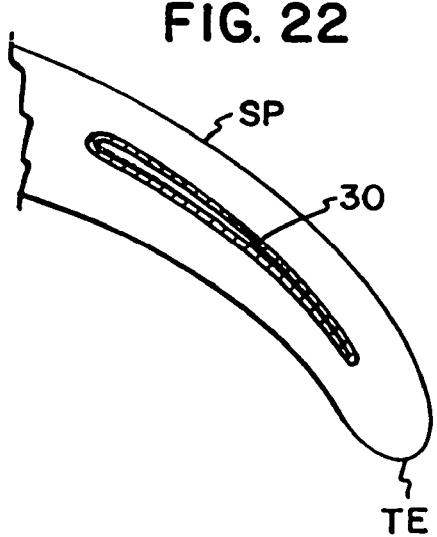
FIG. 22 shows the implant of FIG. 20 in the flattened orientation and implanted in the soft palate.
Figure 23:
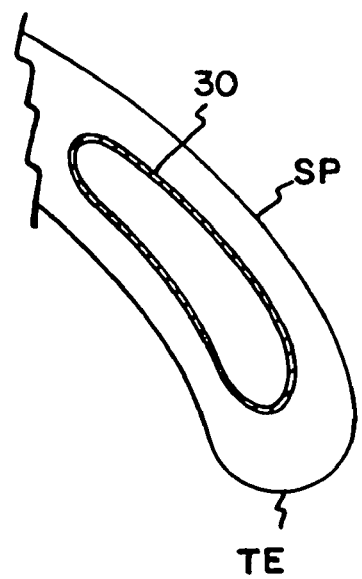
FIG. 23 shows the implant in FIG. 21 in the expanded orientation and implanted in the soft palate.

In the embodiments of FIGS. 20-23, the implant 30 is inserted into the soft palate SP through an incision. The implant 30 has an oval shape to cause deformation of the geometry of the soft palate SP. Prior to implantation, the implant 30 is preferably formed as a flat oval (FIGS. 20 and 22) for ease of insertion. After implantation, the implant 30 expands to an enlarged oval (FIGS. 21 and 23). While such expansion could be accomplished mechanically (i.e., through balloon expansion), the implant 30 is preferably formed as a shape-memory alloy (such as nitinol) which expands to the enlarged shape in response to the warmth of the body. In addition to changing the aerodynamics of the soft palate SP, the implant 30 can be constructed with a mass and stiffness as desired to alter the spring and mass components of the spring-mass system of FIG. 5.

The foregoing describes numerous embodiments of an invention for an implant for the soft palate to alter a dynamic response of the soft palate. The invention is much less traumatic than prior surgical treatments. Further, the invention permits use of reversible procedures as well as procedures which can be selectively tuned both during surgery and post-operatively. Having described the invention, alternatives and embodiments may occur to one of skill in the art. For example, the strips of FIG. 13 may be encased coiled springs which may be tightened to further stiffen the strips. Such strips may also be hinged segments. It is intended that such modifications and equivalents shall be included within the scope of the following claims.

What is claimed is:

1. A method of treating snoring, comprising treating a patient's snoring by the steps of:
   injecting a polymer into a soft palate of said patient in an area between a hard palate and a trailing edge of said soft palate; and
   adding a stiffening agent to said polymer to alter the flexibility of said polymer with an alteration of said flexibility of said polymer due to said addition occurring after the injection of said polymer into said soft palate; and
   wherein said polymer and said stiffening agent are injected into a space defined by a bladder implanted within the patient's soft palate.

* * * * *